. United States Patent [19]

Delton et al.

[11] Patent Number: 4,892,937

[45] Date of Patent: Jan. 9, 1990

[54] TETRA-SUBSTITUTED ARYL CYCLIC FORMAZAN DYES

[75] Inventors: Mary H. Delton, Honeoye Falls; Shari L. Eiff, Scottsville, both of N.Y.

[73] Assignee: Eastman Kodak Company, Rochester, N.Y.

[21] Appl. No.: 145,341

[22] Filed: Jan. 19, 1988

[51] Int. Cl.$^4$ .................... D06P 50/04; G01N 21/78; G01N 33/20; G01N 33/52
[52] U.S. Cl. ..................................... 534/652; 436/74; 436/79; 436/164
[58] Field of Search .................... 540/469; 534/652

[56] References Cited

U.S. PATENT DOCUMENTS 4,742,010  5/1988  Lin et al. ............................. 436/74

FOREIGN PATENT DOCUMENTS 1057500  11/1983  U.S.S.R. .............................. 540/469

OTHER PUBLICATIONS

"Spectrophotometric Determination of Lithium with TMC-Crownformazane", Sitnikova et al., Zhurnal Analiticheskoi, vol. 37, No. 4, pp. 611–613, Apr. 1982.
"Multidentate Formazans, IV., Oxygen-Containing Macrocyclic Chelants (Cyclo-Tri-, -Tetra-, -Hexa- and -Nona-Decine Systems), with a Cyanoformazan Grouping", Dziomko et al., I, Zhurnal Obshchei Khimii, vol. 51, No. 10, pp. 2324–2331, Oct. 1981.
"Macrocyclic Formazans-Derivatives of (1,11,4,5,7,8)-Dioxa-Tetra-Azacuclotetradecyne", Dziomoko et al., II, Khimiya Geterotsiklicheskikh Soedinenii, No. 8, pp. 1039–1040, Aug. 1979.

Primary Examiner—Floyd D. Higel
Attorney, Agent, or Firm—John R. Everett

[57] ABSTRACT

Novel tetra-substituted aryl cyclic formazan dyes are useful in assaying for Li$^+$.

3 Claims, No Drawings

TETRA-SUBSTITUTED ARYL CYCLIC FORMAZAN DYES

FIELD OF THE INVENTION

The present invention relates to novel dyes and the qualitative and quantitative determination of lithium ions ($Li^+$).

BACKGROUND OF THE INVENTION

Analytical methods for the qualitative and quantitative determination of lithium ion ($Li^+$) are of interest in establishing the levels of therapeutic lithium in humans when lithium-type medications are administered as therapy to overcome manic depressive states in human beings. Such methods require that the lithium be determined in the presence of sodium ion.

A U.S.S.R. Author Certificate No. SU1057500A discloses a material having the formula

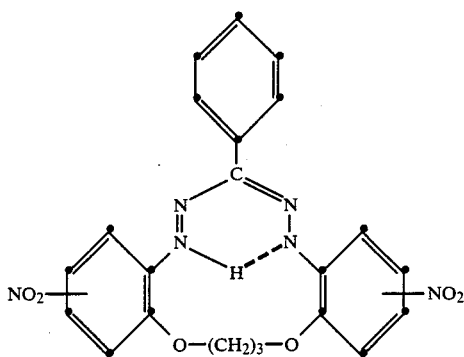

as a chromogenic agent for lithium determinaton. However, following the instructions of the Author Certificate we have been unable to make this compound. Moreover, the same Author Certificate appears to state that compounds of the formula

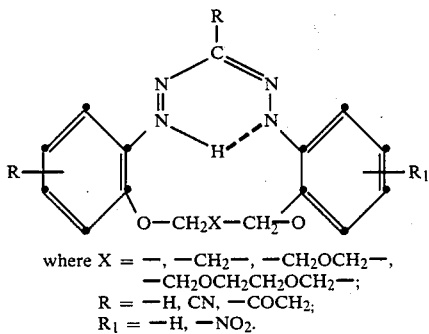

where $X = -, -CH_2-, -CH_2OCH_2-, -CH_2OCH_2CH_2OCH_2-$;
$R = -H, CN, -COCH_2$;
$R_1 = -H, -NO_2$.

are impossible to use as microbiological color reagents. Biological fluids such as blood serum contain concentrations up to 150 milliMolar (mM) of sodium. Presently there are no reagents with which $Li^+$ can be correctly determined in the presence of sodium.

SUMMARY OF THE INVENTION

According to the present invention there is provided a class of novel tetra-substituted aryl cyclic formazan dyes which are useful in the analytical determination of $Li^+$. Such determination can be carried out in the presence of sodium, particularly in the presence of amounts of sodium usually found in biological fluids. The dyes are useful in the quantitative and qualitative analysis of lithium concentrations as low as 0.03 mmolar.

In a preferred embodiment the dyes have the structure

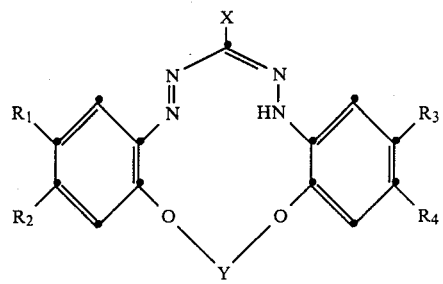

X represents CN or $NO_2$;
Y represents $-CH_2CH_2-$, $-CH_2CH_2CH_2-$ or $-CH_2CH_2-O-CH_2CH_2-$; and
$R_1$, $R_2$, $R_3$ and $R_4$ each independently represent alkyl having up to 12 carbon atoms, halogen (e.g. $Cl^-$, $B_r^-$, $I^-$), alkoxy having up to 12 carbon atoms or $NO_2$.

DETAILS OF THE INVENTION

The analytical method for $Li^+$ comprises the step of complexing $Li^+$ with a dye of the invention. Such method can involve:
(a) preparing a curve which relates lithium concentration to changes in absorbance, at a specified wavelength (e.g. greater than 500 nanometers, preferably in the range 550 to 650, more preferably 600 to 620) nanometers, of a series of solutions comprising the same concentration of a tetra-substituted aryl cyclic formazan dye, a base and varying known concentrations of lithium;
(b) determining the absorbance, at the specified wavelength of a solution containing the (i) same dye and base concentrations as in step (a) and (ii) an aliquot of an aqueous solution containing an unknown concentration of lithium; and
(c) reading the lithium concentration from the curve prepared in step (a) corresponding to the absorbance determined in step (b).

Ideally the method is carried out in pH ranges of 7 to 11.

The method can be used to determine $Li^+$ in the presence of sodium. Accuracy of such a determination can be enhanced by adding to the solution of (a) above an amount of sodium expected in the unknown. In biological fluids amounts up to 150 mM should be sufficient. It has been determined that absorbance of solutions containing the dye, the base, and sodium ion in concentrations up to 150 millimoles/liter (mM/L), is constant. See Table III. Therefore, shifts caused by the presence of $Li^+$ can be determined in the presence of sodium. This also demonstrates the high selectivity of the dyes of this invention for lithium as compared to sodium.

Useful bases which can be used in the method include organic and inorganic material such as morpholine, triethylamine, ammonium hydroxide and TRIS buffer.

Representative dyes of this invention are listed in the following Table I.

TABLE I

| Dye No. | X | Y | R₁ |
|---|---|---|---|
| 1 | CN | —CH₂CH₂CH₂— | OCH₃ |
| 2 | CN | —CH₂CH₂CH₂— | CH₃O—C₆H₄O |
| 3 | CN | —CH₂CH₂CH₂— | C₄H₉ |
| 4 | CN | —CH₂CH₂CH₂— | C₆H₁₃—O—C₆H₄—O |

| Dye No. | R₂ | R₃ | R₄ |
|---|---|---|---|
| 1 | NO₂ | OCH₃ | NO₂ |
| 2 | NO₂ | CH₃OC₆H₄O | NO₂ |
| 3 | NO₂ | C₄H₉ | NO₂ |
| 4 | NO₂ | C₆H₁₃OC₆H₄—O | NO₂ |

The dyes of the invention are prepared according to scheme I or scheme II, infra.

The following examples illustrate the procedures used to make the compounds of this invention.

EXAMPLE 1

Dyes 1 and 3 of Table I were made using reaction scheme I as exemplified in the described actual preparation.

PREPARATION OF DYE 3, TABLE I

Step 1

A stirred solution of p-n-butylphenol (30.0 g, 0.22 mole) in 400 mL CH₂Cl₂ in a 500 mL Erlenmeyer flask was cooled to 5° C. in an ice/water bath. To this, a solution of HNO₃ (conc, 16 mL) in 20 mL of H₂O was added slowly enough to maintain a temperature of 5° C. After a further 15 minutes, the reaction flask was put in the refrigerator (8° C.) for 3 hours.

The product was isolated by a normal ether extraction affording a yellow oil, which thin layer chromatography (ligroin) indicated to be two components. The mixture was purified with column chromatography using ligroine as eluant.

Step 2

A 1000 mL, three-necked, round bottom flask, was equipped with an overhead stirrer, condenser, and N₂ inlet. 4-n-butyl-2-nitrophenol (15 g, 0.077 mole) was added followed by 250 mL of DMF. The mixture was stirred. NaH (2.2 g, 0.09 mole) was slowly added with good stirring. The reaction mixture turned very orange. The mixture was heated at 70° C. for 30 minutes; then 1,3-dichloropropane (4.3 g, 0.038 mole) was combined with a minimal amount of DMF (15 mL) and added to the reaction mixture through the top of the condenser. The mixture was heated to 130° C. and there maintained for 18 hours.

The reaction mixture was passed into a one-necked, round bottom flask. Most of the DMF was stripped on a rotoevaporator leaving an orange oil. The product was isolated by pouring the oil into 600 mL of water and extracting the oil into CH₂Cl₂/ether, followed by a hexane wash.

Step 3

The product of Step 2 was combined with 150 mL of dry tetrahydrofuran and 0.5 g of 10% palladium on carbon in a Parr bottle. The bottle was charged with 46 psi of hydrogen and reduced on a Parr shaker. After 2 hours, the reaction consumed 20 psi of hydrogen, and the reaction mixture changed from yellow to a colorless solution. Thin layer chromatography (CH₂Cl₂) indicated the reaction was complete. The reaction mixture was filtered through a sintered glass funnel filled with a layer of Na₂SO₄ atop a pad of celite to remove the palladium on carbon. The pad was washed with THF, and strip filtered on the rotoevaporator.

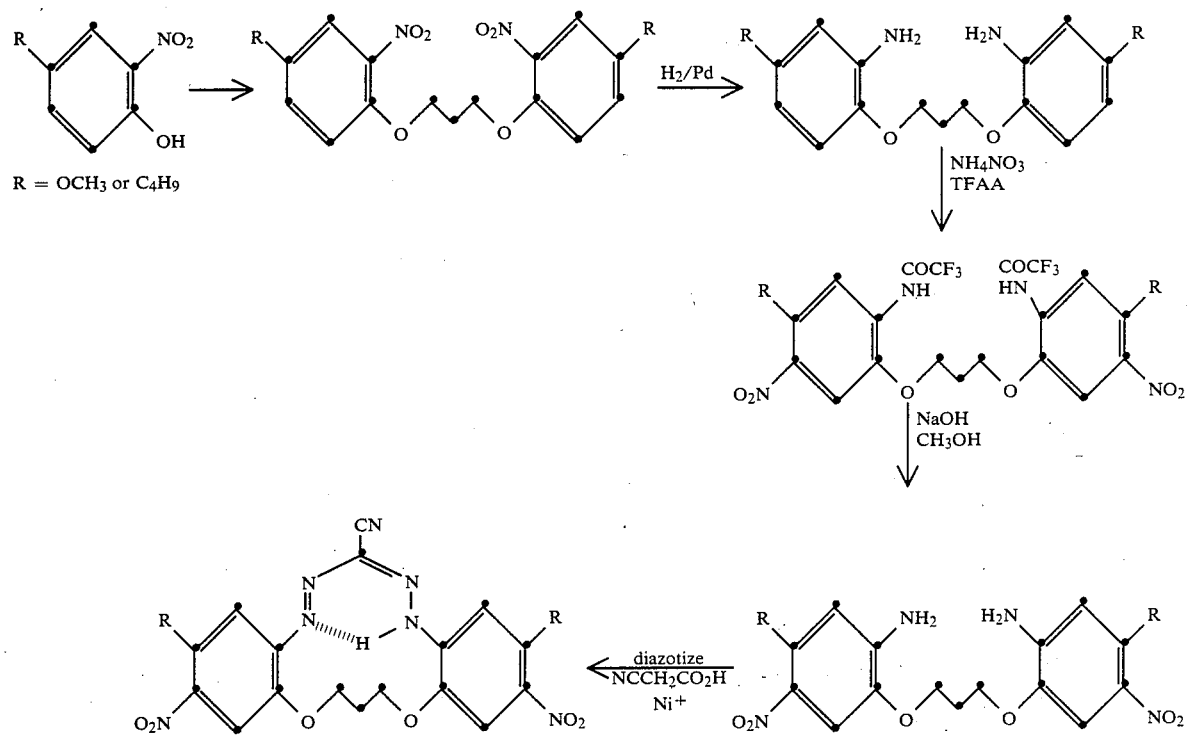

SCHEME I

R = OCH₃ or C₄H₉

Step 4

The product of Step 3 1 (2.1 g) was combined with 10 mL of $CHCl_3$ in a 100 mL round bottom flask equipped with a stirring bar, short condenser, and $N_2$ inlet. $NH_4NO_3$ (0.9 g, 0.01 mole), followed by the trifluoroacetic anhydride (25 mL, 0.176 mole) was added to the solution. A white solid precipitate formed, making stirring difficult. Continued addition of the anhydride made stirring easier. After complete addition, the suspension was stirred for 10 minutes, followed by the addition of 25 mL of $CHCl_3$. After 3 hours, a solution was obtained which was stirred about 20 hours.

The solution was poured into about 800 mL of $H_2O$ and the product was extracted with a $CH_2Cl_2$/ether mixture.

Step 5

The product of Step 4 (1.88 g) was combined with 10 mL of methanol in a 125 mL Erlenmeyer flask equipped with a stirring bar. Stirring slowly, 40 mL of 10% NaOH was added to form a solution. The solution was stirred for 16 hours. A solid formed that was collected and air dried.

The solid was purified by dissolving it in acetone and slowly adding 1.5 times the volume of water. A fine precipitate resulted with stirring and scratching. The precipitate was filtered and dried.

Step 6

A stirred solution of cyanoacetic acid (0.43 g, 0.005 mole), and nickelous nitrate (0.5 g, template) in 100 mL 10% aq. pryidine was cooled to 0° C. in an ice/$CH_3OH$ bath. A solution of the product of Step 5 (0.46 g, 0.001 mole) in 10 mL formic acid, was chilled to 0° C. in an ice/$CH_3OH$ bath and diazotized with nitrosyl sulfuric acid (0.31 mL, 0.002 mole). The diazotized solution was added to the cyanoacetic acid solution with a color change from pale blue to deep red. The mixture was stirred an additional hour at 0° C. and then poured over a liter of ice water and acidified with concentrated HCl to a pH of 3. The reaction mixture was placed in the refrigerator overnight to yield a very fine precipitate. It was filtered, washed well with $H_2O$ and dried. Thin layer chromatography ($CH_2Cl_2$) indicated desired product dye 3.

Dye 3 was purified by eluting it though a short column of silica with 75/25 $CH_2Cl_2$/hexane until color no longer came off the column to afford 157 mg (30%) of pure compound: mp 251°–252° C., $^1H$ NMR ($CDCl_3$) δ 0.95 (t, 6H), 1.15–1.6 (m, 8H), 2.45 (t, 2H), 2.9 (t, 4H), 4.5 (t, 4H), 7.6 (s, 2H), 7.82 (s, 2H), 15.7 (s, NH). Anal. Calcd for $C_{25}H_{29}N_7O_6$: C, 57.4; H, 5.5. Found: C, 57.6; H, 5.7. HRMS, Calcd for $C_{25}H_{29}N_7O_6$: 523,2179. Obsvd: 523,2216.

Compound 1 was made using Scheme I with the appropriately substituted nitrophenol in Step 1. Dye 1 $^1H$ NMR ($CDCl_3$) δ 2.4 (m, 2H), 3.75 (s, 6H), 4.44 (bt, 4H), 6.9 (s, 8H), 7.42 (s, 2H), 7.60 (s, 2H), 15.36 (s, NH). Anal. Calcd for $C_{19}H_{17}N_7O_8$: C, 48.4; H, 3.6; N, 20.8. Found: C, 47.9; H, 3.7; N, 19.2.

EXAMPLE 2

Dyes 2 and 4 were made according to reaction scheme II and the accompanying preparation.

SCHEME II

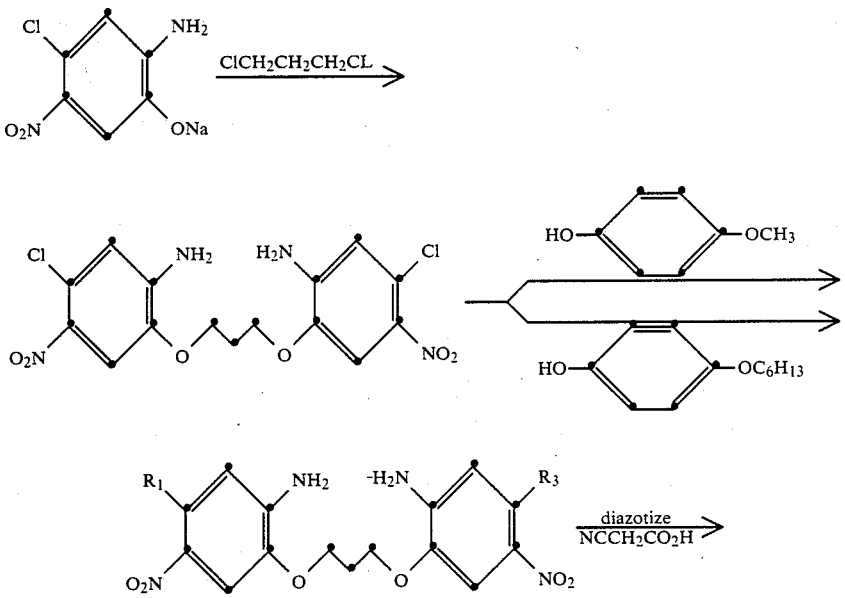

SCHEME II

-continued

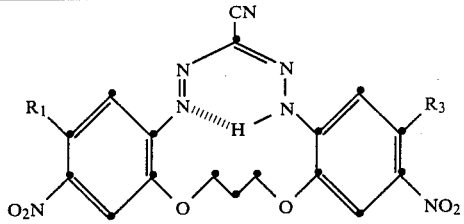

Dye 2 R$_1$ = R$_3$ = OC$_6$H$_4$OCH$_3$
Dye 4 R$_1$ = R$_3$ = OC$_6$H$_4$OC$_6$H$_{13}$

PREPARATION OF METHOXYPHENOXY-NITRO-CYANO-FORMAZAN, (DYE 2)

Step 1

1,3-Bis(2-amino-4-chloro-5-nitrophenoxy)propane was prepared from 2-amino-4-chloro-5-nitrophenol (18.9 g, 0.10 mole) and 1,3-dichloropropane (6.2 g, 0.055 mole) in a manner similar to that used in Step 2 of Example 1 above. The crude reaction mixture was poured into a large volume of water yielding a solid. The solid was purified by dissolving it in acetone and slowly adding 1.5 times the volume of water. A fine precipitate results with stirring and scratching. The precipitate was filtered and dried.

Step 2

A 100 mL three-necked, round bottom flask was fitted with a condenser, stirring bar, N$_2$ inlet and oil bath. With good stirring, p-methoxyphenol (6.21 g, 0.05 mole) followed by 20 mL of dry pyridine was added to the flask to obtain a solution. Potassium-t-butoxide (5.7 g, 0.05 mole) was then added and the solution changed from tan to pale green. Stirring was continued for 15-20 minutes. The condenser was replaced with a distillation head, and using an aspirator, t-bityl alcohol (bp 83° C.), which was generated, was removed. Again, the distillation head was replaced with a condenser. The compound in Step 1 (8.8 g) was added and the mixture was heated at 110° C. overnight (17 hours).

The resulting brown solution was poured into a one-necked, round bottom flask. Pyridine was removed using a rotoevaporator leaving a brown tacky material. The material was dissolved in 1:1 CH$_2$Cl$_2$:ether. A very dark solid precipitate was removed by filtration. The filtrate was washed with H$_2$O and a saturated NaCl solution and dried over Na$_2$SO$_4$. The solvent was removed on the rotoevaporator, leaving a yellow solid.

Step 3

The diamine (1 mmol) prepared in Step 2 above was diazotized using acetic acid/proprionic acid (5:1) as the diazotization solvent along with NaNO$_2$ (0.14 g, 0.002 mole)/conc HCl (0.6 mL). The bis-diazonium ion was coupled with cyanoacetic acid as in the preparation of dye 3.

Dye 2 was isolated as a microcrystalline deep red solid that was purified by chromatography (11%) mp>200° C.; FDMS, 665 (M+); $^1$H NMR (CD$_2$Cl$_2$) δ 2.32 (m, 2 H), 3.70 (s, 6 H), 4.40 (t, 4H), 6.82 (bs, 8H), 7.38 (s, 2H), 7.55 (s, 2H), 15.4 (s, NH).

Dye 4 was isolated by extraction (CH$_2$Cl$_2$) and purified by chromatography (CH$_2$Cl$_2$) to give a waxy red oil (30%): FDMS, 295 (M+); $^1$H NMR (CDCl$_3$) δ 0.91 (m, 6H), 1.15-1.9 (m, 16H), 2.4 (m, 2H), 3.95 (t, 4H), 4.49 (t, 4H), 6.92 (s, 8H), 7.48 (s, 2H), 7.64 (s, 2H), 15.5 (s, NH). ANAL. Calcd for C$_{41}$H$_{45}$N$_7$O$_{10}$: C, 61.9; H, 5.7; N, 12.3. Found: C, 62.3; H, 5.8; N, 11.9.

The method of this invention is also practiced with a dry analytical element. A variety of different elements, depending on the method of assay, can be prepared in accordance with the present invention. Elements can be configured in a variety of forms, including elongated tapes of any desired width, sheets, slides or chips. The simplest element can be composed of an absorbent carrier material, for example, a thin sheet of a self-supporting absorbent or bibulous material, such as filter paper or strips, which contains the dyes of this invention.

The elements can have two or more discrete zones, either in the same layer or superimposed. At least one of the zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, reagents and reaction products (for example, color dyes) can pass or be transported between superposed regions of adjacent zones. In other words, when the element is contacted with fluid, all reagents of the analytical composition become mixed and can readily move within the element as a composition. Preferably, each zone is a separately coated layer, although two or more zones can be separate areas in a single layer of the element. Besides the references noted above, suitable element components are described also, for example in U.S. Pat. Nos. 4,042,335 (issued Aug. 16, 1977 (to Clément), 4,132,528 (issued Jan. 2, 1979 to Eikenberry et al), and 4,144,306 (issued Mar. 13, 1979 to Figueras).

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), 4,270,920 (issued June 2, 1981 to Kondo et al) and 4,312,834 (issued Jan. 26, 1982 to Vogel et al).

Preferably, the absorbent carrier material is a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters, polycarbonates, cellulose esters and others known in the art.

The porous spreading zone can be prepared from any suitable fibrous or non-fibrous material or mixtures of either or both. The void volume and average pore size of this zone can be varied depending upon the use intended.

Useful spreading zones can be prepared using fibrous materials, either mixed with a suitable binder material or woven into a fabric, as described in U.S. Pat. No. 4,292,272 (issued Sept. 29, 1981 to Kitajima et al), polymeric compositions or particulate materials, for example, beads bound together with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760. It is desirable that the spreading zone be isotropically porous, meaning that the porosity is the same in each direction in the zone as caused by interconnected spaces or pores between particles, fibers or polymeric strands.

The method can be manual or automated. In general, in using the dry elements, a $Li^+$ determination is made by taking an element from a supply roll, chip packet or other source and physically contacting it with a sample (for example, up to 200 $\mu$l) of the liquid to be tested so that the sample and reagents within the element become mixed. Such contact can be accomplished in any suitable manner, for example, by dipping or immersing the element into the sample or, preferably, by spotting the element by hand or machine with a drop of the sample with a suitable dispensing means.

The following examples illustrate the use of the dyes of this invention to assay $Li^+$.

EXAMPLE 3

Determination of the Concentration of an Unknown Lithium Ion Solution in the Absence of Sodium Ion A standard calibration curve which relates the absorbance (at 612 nm) of the formazan dye solution and concentrations of lithium ion ($Li^+$) was generated from the following measurements.

A $6.7 \times 10^{-5}$M solution of dye 2 of Table I in 10% aqueous dioxane was made up by dissolving the appropriate amount of dye in the aqueous dioxane in a volumetric flask. A 3.0 ml aliquot of this solution was transferred to a 1 cm curvette and 0.05 ml of triethylamine was added. A reference solution of 3.0 ml of 10% aqueous dioxane containing 0.05 ml or triethylamine was used in the reference curvette for further absorbance measurements.

In separate measurements, the absorbance (at 612 nm) of the above-mentioned dye and base solution together with 0.05 ml of each of six known aqueous lithium chloride solutions were recorded. The six lithium chloride solutions and resulting final $Li^+$ concentrations that were used are indicated below.

a. 0.05 ml of 0.02M LiCl to give 0.323 mM $Li^+$
b. 0.05 ml of 0.03M LiCl to give 0.484 mM $Li^+$
c. 0.05 ml of 0.04M LiCl to give 0.645 mM $Li^+$
d. 0.05 ml of 0.05M LiCl to give 0.806 mM $Li^+$
e. 0.05 ml of 0.065M LiCl to give 1.048 mM $Li^+$
f. 0.05 ml of 0.075M LiCl to give 1.210 mM $Li^+$ The absorbances for each of the above known $Li^+$ concentrations are shown in Table II, along with solutions of lower concentration used to determine a lower detection limit for $Li^+$.

TABLE II

| Detection Limit of $Li^+$ Using $6.7 \times 10^{-5}$ M Dye 2, (Table I) and Triethylamine in 10% Aqueous Dioxane ||
|---|---|
| Conc $Li^+$ (mM) | Abs (612 nm) |
| 0.0322 | 0.521 |
| 0.2419 | 0.893 |
| 0.3226 | 0.993 |
| 0.4839 | 1.110 |
| 0.6452 | 1.200 |
| 0.8065 | 1.227 |
| 1.0484 | 1.320 |
| 1.2097 | 1.352 |

The concentration of $Li^+$ in an unknown solution was determined in the following way:

a. 0.05 ml of the unknown solution was added to 3.05 ml of the above-mentioned dye and base solution and the absorbance at 612 nm recorded.
b. from the standard calibration curve, the $Li^+$ concentration that corresponds to this measured absorption was read.

Table II shows that concentrations as low as 0.0322 mM can be determined using the dyes of this invention.

All the dyes of Table I can be used according to this example for $Li^+$ determinations.

EXAMPLE 4

This example was designed to determine the effect of concentrations of sodium ion (in the physiologically important range of 120–150 mM) on the measurement of $Li^+$.

This experiment was run with solutions which contained different relative concentrations of $Li^+$ and sodium ion but the same concentrations of dye 2 ($5.4 \times 10^{-5}$M) and base. The absorbances of these solutions were measured and the data are shown in Table III.

TABLE III

| Solution No. | $Li^+$ (mM) | $Na^+$ (mM) | Abs (612 nm) |
|---|---|---|---|
| 1 | 1.08 | 0 | 1.175 |
| 2 | 1.08 | 120 | 1.183 |
| 3 | 1.08 | 133 | 1.164 |
| 4 | 1.08 | 150 | 1.158 |
| 5 | 0 | 120 | 0.720 |
| 6 | 0.308 | 133 | 0.960 |

These results indicate that $Li^+$, in the physiological range of 0.3 to 1.0 mM, can be determined in the presence of as much as 150 mM $Na^+$.

EXAMPLE 5

Determination of the Concentration of Unknown $Li^+$ Concentrations in the Presence of $Na^+$ Since the absorbance due to $Li^+$ is unaffected within the experimental error of measurement in the presence of sodium ion in the range of 120 mM–150 mM (see Table III) Li+ was determined in the presence of this range on concentrations of Na+ as follows.

A $6.7 \times 10^{-5}$M solution of dye 4 of Table I in 30% aqueous dioxane was made up by dissolving the appropriate number of milligrams of dye in the aqueous dioxane in a volumetric flask. A 2.4 ml aliquot of this solution was transferred to a 1 cm curvette and 0.05 ml of morpholine or triethylamine was added along with 0.20 ml or 2M sodium chloride and 0.3 ml of water to give a standard dye solution which contained 133 mM Na+. A reference solution of 3.0 ml of 10% aqueous dioxane containing 0.05 ml or morpholine or triethylamine was used in the reference curvette for further absorbance measurements.

In separate measurements, the absorbance (at 612 nm) of the above-mentioned dye and base and NaCl solution together with 0.05 ml of each of the five known aqueous LiCl solutions were recorded as in example 3. The data obtained was plotted to give a standard calibration curve in the presence of sodium ion.

From this new standard calibration curve, the concentration of an unknown lithium solution that contains Na+ in the concentration range of 120-150 mM/L (such as that encountered in human serum) can be determined by measuring the absorbance and reading the concentration from the calibration curve in the same manner as that used in example 1.

EXAMPLE 6

An element was prepared comprising a poly(ethylene terephthalate) support; a reagent layer comprised of gelatin, Triton X-100 surfactant (Rohm & Haas, Philadelphia, Pa.), tris(hydroxymethyl) aminomethane buffer pH 8.5 (Sigma Chemical Co., St. Louis, Mo.) and Dye 2, coated in diethyl lauramide or dioctyphenyl phosphonate; a subbing layer comprised of poly(N-isopropylacrylamide); and a spreading layer comprised of titanium dioxide, cellulose acetate, Estane ™ (B. F. Goodrich, Cleveland, Ohio) and Triton X-100.

This coating was then spotted with several drops of a 1 molar solution of lithium chloride in TRIS buffer, pH 8.5. A color change from red to blue was seen, indicating that this element is suitable for the qualitative determination Li+.

The invention has been described in detail with particular reference to preferred embodiments thereof, but it will be understood that variations and modifications can be effected within the spirit and scope of the invention.

We claim:

1. A dye having the structure

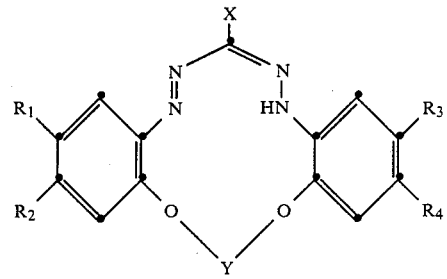

wherein
X represents CN or $NO_2$;
Y represents $CH_2CH_2$, $CH_2CH_2CH_2$, or $CH_2CH_2$—O—$CH_2CH_2$; and
$R_1$, $R_2$, $R_3$ and $R_4$ each independently represent butyl, halogen, alkoxy or $NO_2$.

2. A dye according to claim 1 wherein $R_1$, $R_2$, $R_3$ and $R_4$ each independently represent $NO_2$, methoxy, butyl, methoxyphenoxy or hexyloxyphenoxy.

3. A dye according to claim 1 selected from Table I as follows:

TABLE I

| Dye No. | X | Y | $R_1$ |
|---|---|---|---|
| 1 | CN | —$CH_2CH_2CH_2$— | $OCH_3$ |
| 2 | CN | —$CH_2CH_2CH_2$— | $CH_3O$—$C_6H_4O$ |
| 3 | CN | —$CH_2CH_2CH_2$— | $C_4H_9$ |
| 4 | CN | —$CH_2CH_2CH_2$— | $C_6H_{13}$—O—$C_6H_4$—O |

| Dye No. | $R_2$ | $R_3$ | $R_4$ |
|---|---|---|---|
| 1 | $NO_2$ | $OCH_3$ | $NO_2$ |
| 2 | $NO_2$ | $CH_3OC_6H_4O$ | $NO_2$ |
| 3 | $NO_2$ | $C_4H_9$ | $NO_2$ |
| 4 | $NO_2$ | $C_6H_{13}OC_6H_4$—O | $NO_2$ |

* * * * *